US012551653B2

(12) United States Patent
Panesar

(10) Patent No.: US 12,551,653 B2
(45) Date of Patent: Feb. 17, 2026

(54) METHODS OF MAKING SLEEVED HYDROPHILIC CATHETER PRODUCTS

(71) Applicant: Hollister Incorporated, Libertyville, IL (US)

(72) Inventor: Satwinder S. Panesar, Foxford (IE)

(73) Assignee: Hollister Incorporated, Libertyville, IL (US)

( * ) Notice: Subject to any disclaimer, the term of this patent is extended or adjusted under 35 U.S.C. 154(b) by 53 days.

(21) Appl. No.: 18/565,004

(22) PCT Filed: May 5, 2022

(86) PCT No.: PCT/US2022/027858

§ 371 (c)(1),
(2) Date: Nov. 28, 2023

(87) PCT Pub. No.: WO2022/256114

PCT Pub. Date: Dec. 8, 2022

(65) Prior Publication Data

US 2024/0245883 A1 Jul. 25, 2024

Related U.S. Application Data

(60) Provisional application No. 63/197,216, filed on Jun. 4, 2021.

(51) Int. Cl.
*A61M 25/00* (2006.01)
*B65B 5/04* (2006.01)

(52) U.S. Cl.
CPC ...... *A61M 25/0009* (2013.01); *A61M 25/002* (2013.01); *B65B 5/04* (2013.01)

(58) Field of Classification Search
CPC ........ B65B 5/02; B65B 5/04; A61M 25/0009; A61M 25/002
See application file for complete search history.

(56) References Cited

U.S. PATENT DOCUMENTS

| | | | |
|---|---|---|---|
| 3,035,691 A | 5/1962 | Rasmussen | |
| 3,817,248 A | 6/1974 | Buckles | |
| 4,026,296 A | 5/1977 | Stoy | |
| 4,136,681 A | 1/1979 | Hon | |
| 4,906,237 A | 3/1990 | Johansson | |
| 4,976,720 A * | 12/1990 | Machold | A61M 25/09033 604/913 |
| 5,130,124 A | 7/1992 | Merianos | |
| 5,328,848 A | 7/1994 | Fong | |

(Continued)

FOREIGN PATENT DOCUMENTS

| | | |
|---|---|---|
| CN | 103301551 A | 9/2013 |
| EP | 1131112 B1 | 2/2003 |

(Continued)

OTHER PUBLICATIONS

International Search Report and Written Opinion issued in International App. No. PCT/US2022/027858, mailed on Sep. 9, 2022.

(Continued)

*Primary Examiner* — Andrew M Tecco
*Assistant Examiner* — Nicholas E Igbokwe
(74) *Attorney, Agent, or Firm* — Cook Alex Ltd.

(57) ABSTRACT

Methods of making sleeved hydrophilic urinary catheters (10).

16 Claims, 4 Drawing Sheets

(56) References Cited

U.S. PATENT DOCUMENTS

| | | | | |
|---|---|---|---|---|
| 5,562,652 | A | 10/1996 | Davis | |
| 5,576,072 | A | 11/1996 | Hostettler | |
| 5,616,119 | A | 4/1997 | Davis | |
| 5,876,663 | A | 3/1999 | Laroussi | |
| 5,895,374 | A | 4/1999 | Roedsten | |
| 6,120,904 | A | 9/2000 | Hostettler | |
| 6,270,902 | B1 | 8/2001 | Tedeschi | |
| 6,528,544 | B2 | 3/2003 | Stern | |
| 6,629,961 | B1 | 10/2003 | Israelsson | |
| 6,848,574 | B1 | 2/2005 | Israelsson | |
| 6,923,936 | B2 | 8/2005 | Swanson | |
| 6,986,868 | B2 | 1/2006 | Madsen | |
| 7,022,651 | B1 | 4/2006 | Lightcap, Jr. | |
| 7,066,912 | B2 | 6/2006 | Nestenborg | |
| 7,282,165 | B2 | 10/2007 | Williams, III | |
| 7,334,679 | B2 | 2/2008 | Givens, Jr. | |
| 7,569,155 | B2 | 8/2009 | Schaefer | |
| 7,770,726 | B2 | 8/2010 | Murray | |
| 7,833,475 | B2 | 11/2010 | Madsen | |
| 8,133,435 | B2 | 3/2012 | Reynolds | |
| 8,177,774 | B2 | 5/2012 | House | |
| 8,267,919 | B2 | 9/2012 | Utas | |
| 8,608,689 | B2 | 12/2013 | Scheller | |
| 8,703,048 | B2 | 4/2014 | Nielsen | |
| 8,747,882 | B2 | 6/2014 | Utas | |
| 8,747,911 | B2 | 6/2014 | Gupta | |
| 8,871,869 | B2 | 10/2014 | Dias | |
| 8,998,882 | B2 | 4/2015 | Knapp | |
| 9,028,858 | B2 | 5/2015 | Nielsen | |
| 9,138,510 | B2 | 9/2015 | Madsen | |
| 9,192,741 | B1 | 11/2015 | Najibi | |
| 9,408,946 | B2 | 8/2016 | Utas | |
| 9,610,384 | B2 | 4/2017 | Belt | |
| 9,801,979 | B2 | 10/2017 | Utas | |
| 9,872,970 | B2 | 1/2018 | Schønfeldt | |
| 10,245,355 | B2 | 4/2019 | Ingber | |
| 10,293,136 | B2 | 5/2019 | Palmer | |
| 10,328,237 | B2 | 6/2019 | Kelly | |
| 10,398,161 | B2 | 9/2019 | Arne | |
| 10,813,676 | B2 | 10/2020 | Shimko | |
| 10,973,573 | B2 | 4/2021 | Asirvatham | |
| 10,982,100 | B2 | 4/2021 | Aizenberg | |
| 10,987,487 | B1 | 4/2021 | Palmer | |
| 11,338,109 | B2 | 5/2022 | Farrell | |
| 2001/0001443 | A1 | 5/2001 | Kayerod | |
| 2002/0026182 | A1 | 2/2002 | Joye | |
| 2002/0045049 | A1 | 4/2002 | Madsen | |
| 2002/0120333 | A1 | 8/2002 | Keogh | |
| 2003/0065292 | A1 | 4/2003 | Darouiche | |
| 2003/0124080 | A1 | 7/2003 | Kawam | |
| 2003/0219475 | A1 | 11/2003 | Truong-Le | |
| 2004/0018228 | A1 | 1/2004 | Fischell | |
| 2004/0060260 | A1 | 4/2004 | Gottlieb | |
| 2004/0074794 | A1 | 4/2004 | Conway | |
| 2004/0256264 | A1 | 12/2004 | Israelsson | |
| 2005/0015076 | A1 | 1/2005 | Giebmeyer | |
| 2005/0043715 | A1* | 2/2005 | Nestenborg | A61M 25/002 206/439 |
| 2005/0055044 | A1 | 3/2005 | Kangas | |
| 2005/0061698 | A1 | 3/2005 | Delaney | |
| 2005/0109648 | A1 | 5/2005 | Kerzman | |
| 2005/0182359 | A1* | 8/2005 | Chin | A61M 25/0075 604/96.01 |
| 2005/0214376 | A1 | 9/2005 | Faure | |
| 2006/0051384 | A1 | 3/2006 | Scholz | |
| 2006/0095015 | A1 | 5/2006 | Hobbs | |
| 2006/0155250 | A1 | 7/2006 | Endo | |
| 2006/0163097 | A1 | 7/2006 | Murray | |
| 2006/0196783 | A1 | 9/2006 | Bruun | |
| 2006/0263404 | A1 | 11/2006 | Nielsen | |
| 2007/0088330 | A1* | 4/2007 | House | A61M 25/0111 604/327 |
| 2007/0225649 | A1* | 9/2007 | House | A61M 25/002 604/171 |
| 2007/0239107 | A1 | 10/2007 | Lundberg | |
| 2007/0244449 | A1 | 10/2007 | Najafi | |
| 2008/0142038 | A1 | 6/2008 | Kunzler | |
| 2008/0172042 | A1* | 7/2008 | House | A61M 25/0111 604/544 |
| 2009/0012208 | A1 | 1/2009 | Madsen | |
| 2009/0041727 | A1 | 2/2009 | Suzuki | |
| 2009/0171317 | A1 | 7/2009 | Versi | |
| 2009/0214674 | A1 | 8/2009 | Barraud | |
| 2009/0221989 | A1 | 9/2009 | Najafi | |
| 2009/0240214 | A1 | 9/2009 | Conway | |
| 2010/0166809 | A1 | 7/2010 | Northey | |
| 2010/0215643 | A1 | 8/2010 | Clevenger | |
| 2010/0258568 | A1 | 10/2010 | Frederiksen | |
| 2011/0114520 | A1 | 5/2011 | Matthison-Hansen | |
| 2011/0150961 | A1 | 6/2011 | Perry | |
| 2011/0295239 | A1 | 12/2011 | Gustavsson | |
| 2012/0207853 | A1 | 8/2012 | Alimi | |
| 2012/0289942 | A1 | 11/2012 | Becker | |
| 2013/0161208 | A1 | 6/2013 | Gustavsson | |
| 2014/0190846 | A1 | 7/2014 | Belt | |
| 2014/0271351 | A1 | 9/2014 | Nielsen | |
| 2015/0065998 | A1 | 3/2015 | Nielsen | |
| 2015/0105756 | A1 | 4/2015 | O'Brien | |
| 2015/0238726 | A1 | 8/2015 | Terry | |
| 2015/0264935 | A1 | 9/2015 | Chang | |
| 2015/0265801 | A1 | 9/2015 | Rostami | |
| 2015/0273180 | A1 | 10/2015 | Schønfeldt | |
| 2015/0306342 | A1 | 10/2015 | Rostami | |
| 2015/0335854 | A1 | 11/2015 | Dvärsäter | |
| 2016/0129219 | A1 | 5/2016 | Gustavsson | |
| 2016/0143944 | A1 | 5/2016 | Panicheva | |
| 2016/0213880 | A1* | 7/2016 | O'Flynn | A61M 25/002 |
| 2017/0274188 | A1* | 9/2017 | Goto | A61B 17/1204 |
| 2017/0296609 | A1 | 10/2017 | Ellington | |
| 2017/0296610 | A1 | 10/2017 | Ellington | |
| 2017/0312484 | A1 | 11/2017 | Shipley | |
| 2017/0326334 | A1 | 11/2017 | Terry | |
| 2018/0000993 | A1 | 1/2018 | Zhang | |
| 2018/0010038 | A1 | 1/2018 | Greenhill-Hooper | |
| 2018/0021481 | A1 | 1/2018 | Yin | |
| 2018/0221541 | A1 | 8/2018 | Pesika | |
| 2018/0258363 | A1 | 9/2018 | Rhodes | |
| 2019/0083746 | A1 | 3/2019 | Murray | |
| 2019/0105078 | A1 | 4/2019 | Taylor | |
| 2019/0151610 | A1 | 5/2019 | Fletter | |
| 2019/0167849 | A1 | 6/2019 | Mcburney | |
| 2019/0201659 | A1 | 7/2019 | Gustavsson | |
| 2019/0216735 | A1 | 7/2019 | Venkatraman | |
| 2019/0216985 | A1 | 7/2019 | Mcburney | |
| 2019/0224384 | A1 | 7/2019 | Lundahl | |
| 2019/0262647 | A1 | 8/2019 | Havelka-Rivard | |
| 2019/0290805 | A1 | 9/2019 | Kumaraswamy | |
| 2019/0290806 | A1 | 9/2019 | Farrell | |
| 2020/0038535 | A1 | 2/2020 | Montes De Oca | |
| 2020/0054795 | A1 | 2/2020 | Farrell | |
| 2020/0146871 | A1 | 5/2020 | Palmer | |
| 2020/0155261 | A1 | 5/2020 | O'Flynn | |
| 2020/0206139 | A1 | 7/2020 | Williams, III | |
| 2020/0222659 | A1 | 7/2020 | Schertiger | |
| 2020/0338082 | A1 | 10/2020 | Ackler | |
| 2020/0345977 | A1 | 11/2020 | Hickmott | |
| 2020/0391002 | A1 | 12/2020 | Hilton | |
| 2020/0405919 | A1 | 12/2020 | Van Weerd | |
| 2021/0038508 | A1 | 2/2021 | Binyamin | |
| 2021/0059654 | A1* | 3/2021 | Ryan | A61L 31/145 |
| 2021/0138189 | A1 | 5/2021 | Montes De Oca | |
| 2021/0260332 | A1 | 8/2021 | Panesar | |
| 2022/0280751 | A1 | 9/2022 | Farrell | |
| 2022/0387673 | A1 | 12/2022 | Farrell | |
| 2023/0293849 | A1 | 9/2023 | Hughett, Sr. | |

FOREIGN PATENT DOCUMENTS

| | | | |
|---|---|---|---|
| EP | 1312385 | B1 | 2/2006 |
| EP | 1714665 | B1 | 10/2006 |
| EP | 2423127 | A1 | 2/2012 |
| EP | 2468346 | A1 | 6/2012 |
| EP | 2550030 | B1 | 1/2013 |
| EP | 2695636 | A1 | 2/2014 |

(56) References Cited

FOREIGN PATENT DOCUMENTS

| | | | |
|---|---|---|---|
| EP | 3071249 | B1 | 9/2016 |
| WO | 2001005443 | A1 | 1/2001 |
| WO | 2002100455 | A2 | 12/2002 |
| WO | 2003087327 | | 10/2003 |
| WO | 2004075944 | A2 | 9/2004 |
| WO | 2005014055 | A2 | 2/2005 |
| WO | 2005117914 | A2 | 12/2005 |
| WO | 2014074141 | A1 | 5/2014 |
| WO | 2016033234 | A1 | 3/2016 |
| WO | 2017001830 | A1 | 1/2017 |
| WO | 2018022763 | A1 | 2/2018 |
| WO | 2018028831 | A1 | 2/2018 |
| WO | 2018029279 | A1 | 2/2018 |
| WO | 2019014344 | A1 | 1/2019 |
| WO | 2019222644 | A1 | 11/2019 |
| WO | 2021092388 | A1 | 5/2021 |

OTHER PUBLICATIONS

Castro, et al. "Natural deep eutectic systems as alternative nontoxic cryoprotective agents", Cryobiology, 83, 1-12 and 15-26 (2018).

* cited by examiner

METHODS OF MAKING SLEEVED HYDROPHILIC CATHETER PRODUCTS

TECHNICAL FIELD

The present application is the U.S. National Stage Application of PCT Application No. PCT/US2022/027858, filed May 5, 2022, which claims the benefit of and priority to U.S. Provisional Patent Application Ser. No. 63/197,216, filed Jun. 4, 2021, the disclosure of all of which is hereby incorporated herein by reference.

Background

It is known to coat medical devices, such as urinary catheters, with a hydrophilic coating. When the hydrophilic coating is wetted or hydrated with a hydration medium it becomes extremely lubricous. The hydration medium may be, for example, liquid or vapor water or an aqueous solution. The lubriciousness of the hydrophilic coating eases introduction of the device into the body and aids in reducing pain and discomfort associated with such introduction.

In some urinary catheter products, the user directly contacts the urinary catheter with the user's fingers to remove the catheter from the package and inserts it into the urethra. In such products there may be a disadvantage in that the handling of the catheter by the user may introduce microorganisms onto the surface of the catheter which can cause infectious problems after being introduced into the body during catheter insertion. To address this issue, manufacturers have devised systems that include a protective or barrier sleeve surrounding the catheter. In this type of product, the catheter tube is located in a barrier sleeve. The sleeve may loosely fit the diameter of the catheter so that the user may grasp the catheter tube through the sleeve to manipulate the catheter, e.g., remove the catheter from its package and advance the catheter into the urethra. In some products, the distal end of the sleeve may be attached to the drainage member of the catheter and an insertion aid may be attached to or otherwise associated with the proximal end of the sleeve.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a method of making a catheter product that has a sleeve having a cavity wherein at least a portion of a catheter shaft of a urinary catheter is located within the cavity such that the sleeve surrounds the portion of catheter shaft, and a distal portion of the sleeve is attached to a distal portion of the urinary catheter and a proximal portion of the sleeve is attached an introducer aid. The method includes injecting a hydration medium into the cavity of the sleeve, wherein the hydration medium is in contact with the catheter shaft. Additionally, during the injection of the hydration medium, air is vented out of the cavity of the sleeve through at least one vent located at the distal end of the sleeve.

DETAILED DESCRIPTION OF THE ILLUSTRATED EMBODIMENTS

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The present disclosure is directed to methods of making a sleeved hydrophilic urinary catheter assembly wherein the sleeved catheter is packaged and the urinary catheter is ready-to-use right out of the package. That is, while in the package, the hydrophilic outer surface of the catheter tube within the interior cavity of the sleeve is in a hydrated/activated state, so that the catheter is ready-to-use right out of the package.

Figure 1:
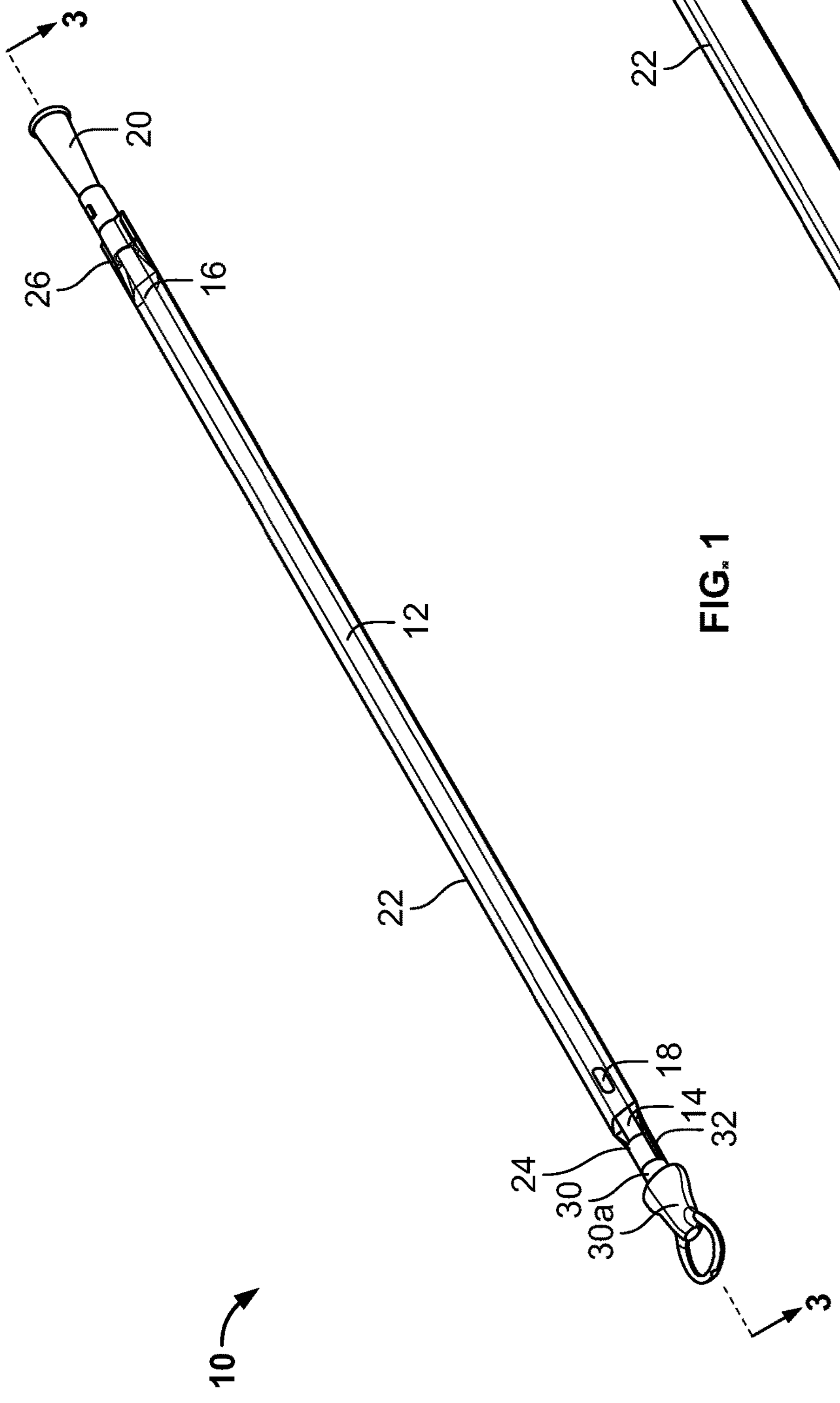
FIG. 1 is a perspective view of a urinary catheter in accordance with the present disclosure.
Figure 2:
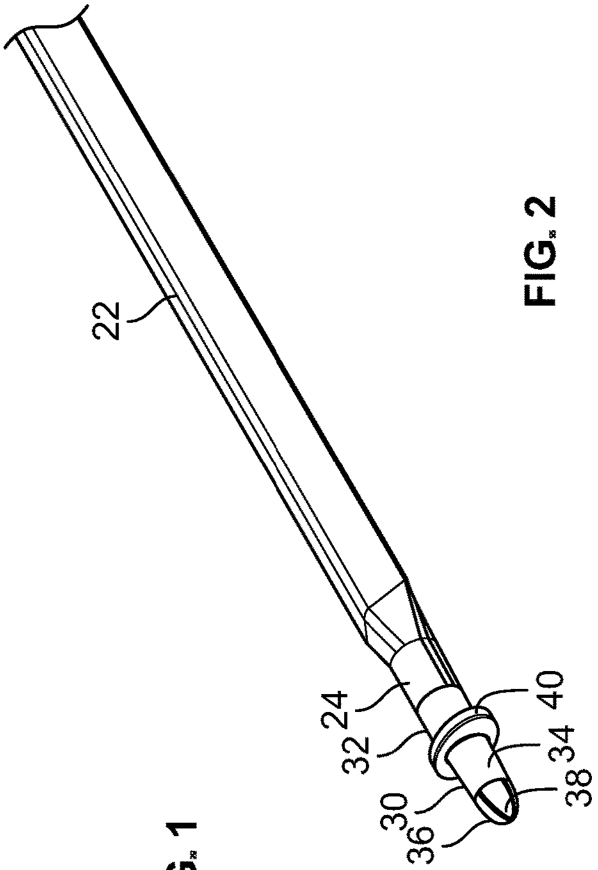
FIG. 2 is partial front perspective view of the proximal end of the urinary catheter of FIG. 1, shown with the protective cap removed.
Figure 3:
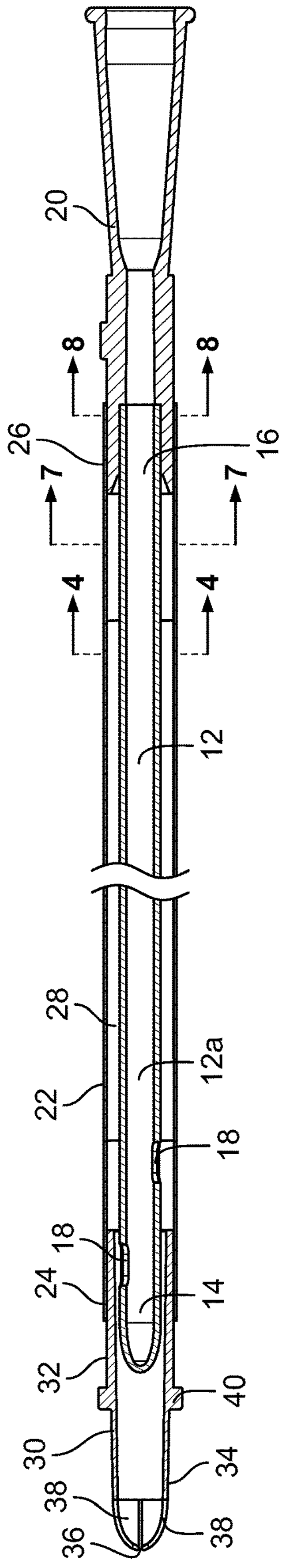
FIG. 3 is a cross-sectional view of the urinary catheter of FIG. 1 shown with the protective cap removed, the cross-section is taken along lines 3-3 of FIG. 1.
Figure 5:
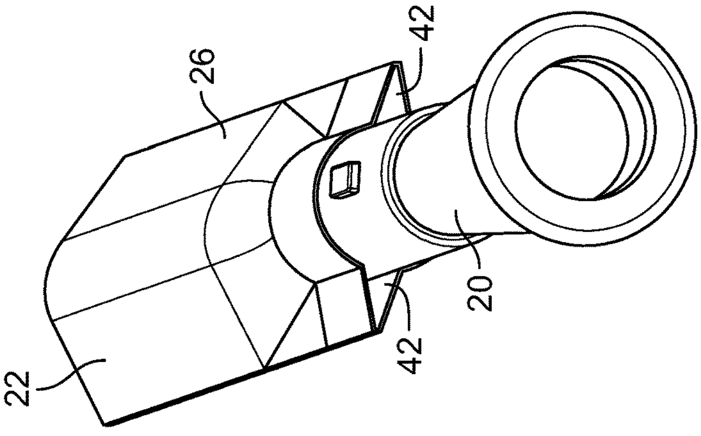
FIG. 5 is partial rear perspective view of the distal end portion of the urinary catheter of FIG. 1.
Figure 4:
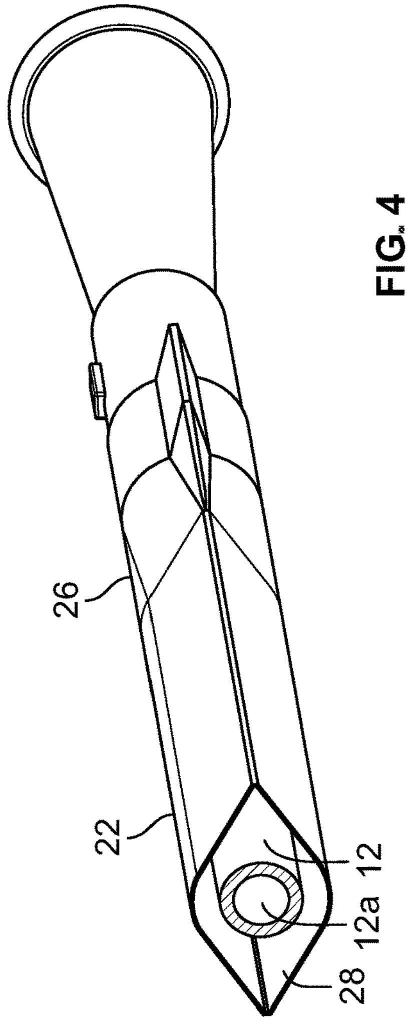
FIG. 4 is a partial cross-sectional view of the distal end portion urinary catheter of FIG. 3, taken along lines 4-4 of FIG. 3.
Figure 7:
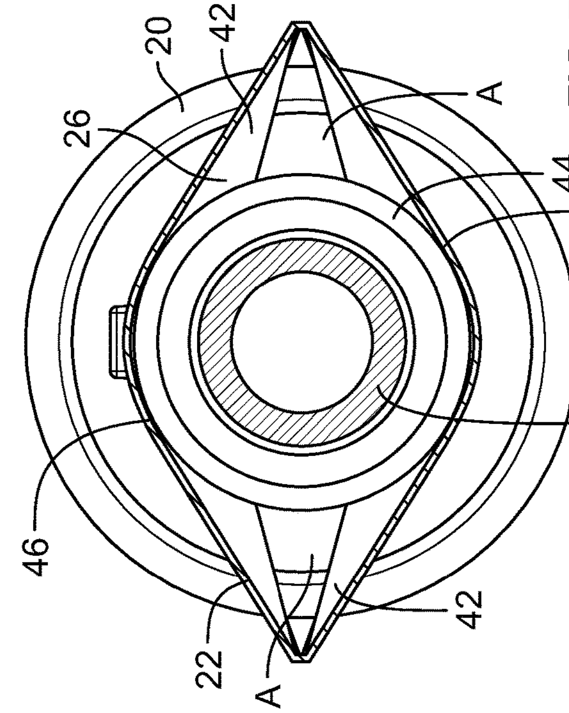
FIG. 7 is a cross-sectional view of the urinary catheter of FIG. 3, taken along lines 7-7 of FIG. 3.
Figure 8:
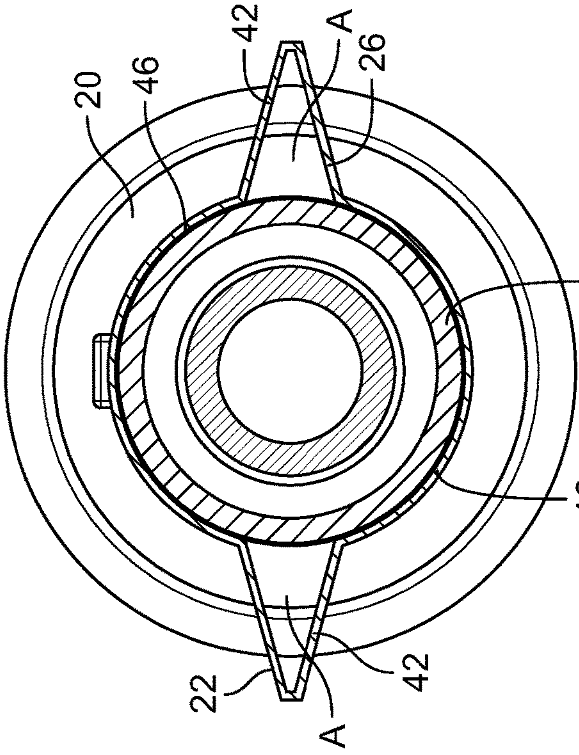
FIG. 8 is a cross-sectional view of the urinary catheter of FIG. 3, taken along lines 8-8 of FIG. 3.
Figure 6:
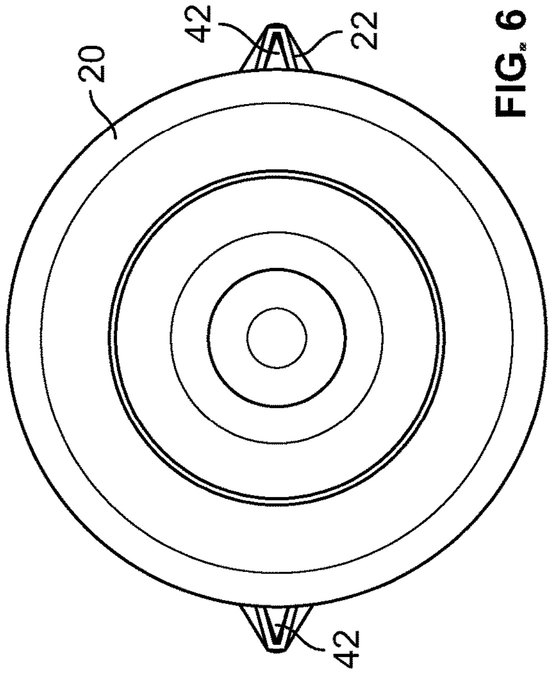
FIG. 6 is a rear elevational view of the urinary catheter of FIG. 1.

FIGS. 1-3 illustrate one embodiment of a urinary catheter 10 in accordance with present disclosure. The catheter 10 includes an elongated catheter tube or shaft 12 having a proximal end portion 14, a distal end portion 16 and a lumen **12*a* (FIGS. 3 and 4). The proximal end portion 14 of the catheter shaft 12 is suitable for insertion into a lumen or a passageway of the body, such as the urethra. The proximal end portion 14 may include drainage holes or eyelets 18 for draining urine from the bladder. Optionally, a drainage member 20 may be associated with the distal end portion 16 of the catheter shaft 12. The drainage member 20 may be a funnel or connector for connecting the shaft 12 to a collection receptacle. The catheter shaft 12** includes an outer hydrophilic surface that becomes lubricious when hydrated or activated by a hydration medium. The outer surface may be, for example, any suitable hydrophilic coating. The hydration medium may be a foamed liquid.

The catheter assembly 10 also includes a sleeve 22, which may be a protective or barrier sleeve, that has a proximal portion 24 and a distal portion 26. The sleeve 22 defines a cavity 28 (FIGS. 3 and 4) that contains at least a portion of the catheter shaft 12 such that the sleeve surrounds the portion of the catheter shaft 12. The sleeve 22 separates and encloses the portion of the catheter shaft 12 from the outside environment. In one embodiment, the sleeve 22 extends over the length of the catheter shaft 12. Optionally, an insertion aid 30 (FIGS. 2 and 3) may be located at the proximal portion 24 of the sleeve 22. When an insertion aid 28 is present, the proximal portion 24 of the sleeve 22 may be attached to a wall or barrel 32 of the insertion aid 30, by for example, welding or adhesive. The distal portion 26 of the sleeve 22 may be attached to the drainage member 20, as will be described in greater detail below. Alternatively, the distal portion 26 of the sleeve 22 could be attached to the distal end portion 16 of the catheter shaft 12.

The sleeve 22 may be made of a flexible material which may be vapor permeable or vapor impermeable, depending on the desired use and packaging. The material of the sleeve 22 may also be liquid impermeable. The sleeve 22 may be formed of any of a variety of thin, flexible polymeric film materials, such as polyethylene, plasticized PVC, or polypropylene, but elastomeric film materials such as polyurethane, and particularly elastomeric hydrogel materials, may be particularly suitable. The thickness of the film from which the sleeve 22 is formed may vary considerably depending on factors such as stretchability and flexibility of the material selected but, in general, the thickness may fall within the range of about 10 to 150 microns, preferably about 13 to 50 microns.

As shown in FIG. 1, optionally, a removable protective cap 30*a* may cover the insertion aid 30. In FIGS. 2 and 3, the urinary catheter 10 is shown without the protective cap 30*a*. The insertion aid 30 includes a proximal portion 34 that defines an introducer tip 36. The introducer tip 36 has a proximal end opening defined by one or more slits between one or more flexible petals 38. The petals 38 may move, bend and/or resiliently deform from the generally closed configuration shown in the figures to an open configuration (not shown) to allow for advancement of the catheter shaft 12 therethrough. The insertion aid 30 may also include an intermediate flange 40 that may contact the user about the urethra opening and act as a stop to limit the insertion of the introducer tip 36.

Turning now to FIGS. 5-8, the urinary catheter 10 may have at least one vent 42 at the distal end of the urinary catheter 10. The vents 42 are in communication with the cavity 28 of the sleeve 22 and allow air to vent/flow from the cavity 28 to the atmosphere outside of the sleeve 22. The vents 42 may be at least partially defined by sleeve 22. In the illustrate embodiment, distal portion 26 the sleeve 22 is attached to select portions 46 of the drainage member 20. In other words, there may be two or more select attachment between the sleeve 22 and drainage member 20. For example, the drainage member 20 may include a barrel 44, wherein the distal portion 26 of the sleeve 22 is attached to select portions 46 of the barrel 44 of the drainage member 20. In the illustrated embodiment, the distal portion 26 of sleeve 22 is not fully attached around the barrel's 44 outer wall and portions of the distal portion 26 of the sleeve 22 are left unattached from the barrel 44. In other words, the distal portion 26 of sleeve 22 may be intermittently attached to the drainage member 20. The vents 42 are defined by or between the distal portion 26 of the sleeve 22 and the drainage member 20.

In an alternative embodiment, the sleeve 22 may be partially attached to the catheter shaft 12 instead of a drainage member 20. In such embodiments, the vents may be defined by or between the distal portion 26 of the sleeve 22 and the catheter shaft 12. In yet another alternative, the vents 42 may be fully defined by the sleeve or in the sleeve wall. For example, the vents may be slits, perforations, micro-perforations, or other suitable openings in the sleeve wall. When the vents 42 are fully defined by the sleeve, the distal portion 26 of the sleeve may be fully attached to the drainage member 20 or the catheter shaft 12.

In the illustrate embodiment, the urinary catheter 10 includes two vents 42. In other embodiments, the urinary catheter 10 may include one vent 42 or more than two vents 42. Also, in the illustrated urinary catheter, the vents 42 are shown to have a substantially equal size and shape. However, in an alternative, the vents 42 could have different sizes and shapes. Each of the vents 42 has a vent opening area A. In the illustrated embodiment, the vent opening area is defined by the unattached area between the distal portion 26 of the sleeve 22 the barrel 44 of the drainage member 20. The combined area of the vent opening areas A may be between about 30 square millimeters and about 40 square millimeters. Thus, in the illustrated embodiment, each vent 42 may have an opening area A of between about 15 square millimeters and about 20 square millimeters.

Figure 9:
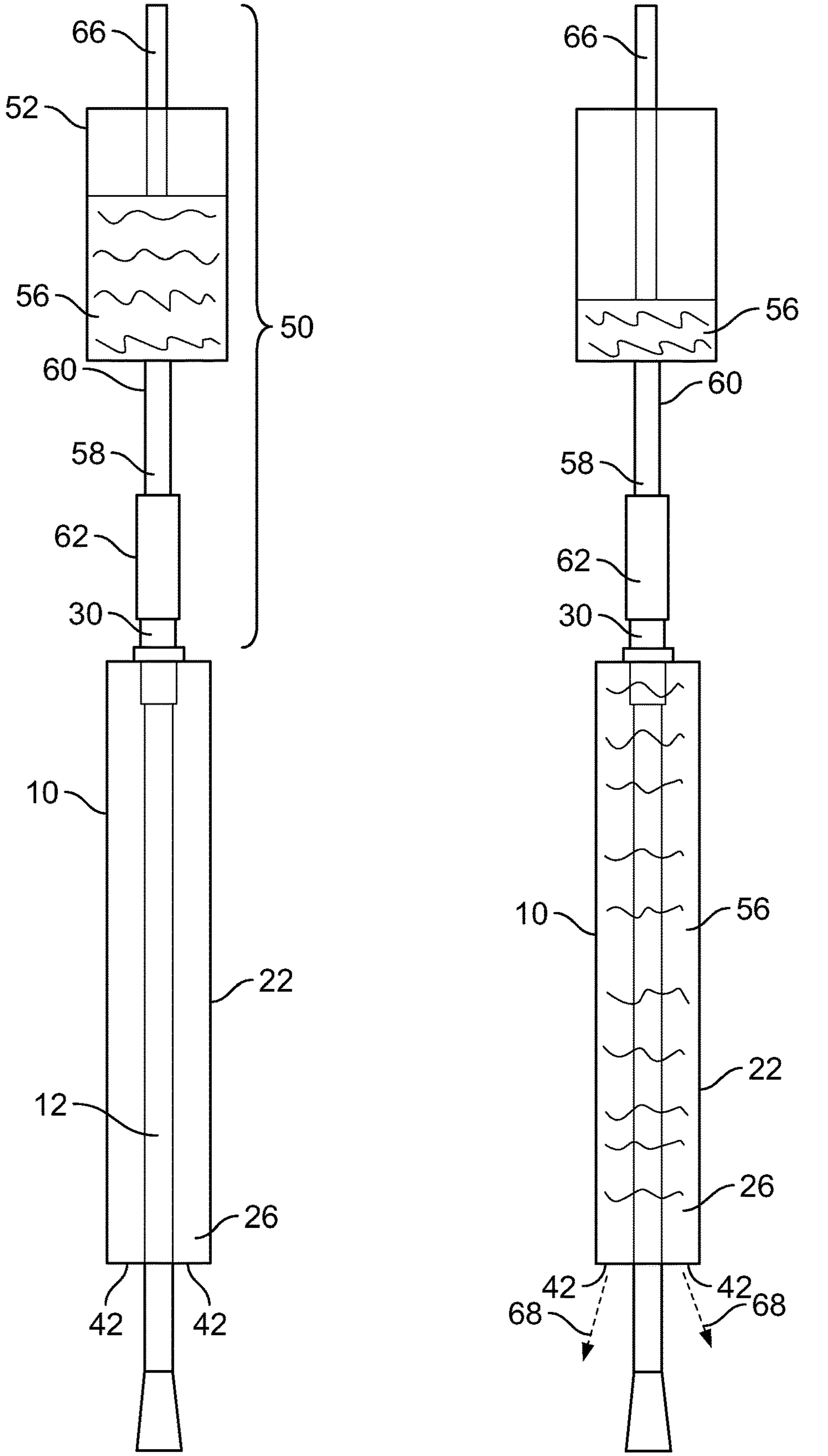
FIG. 9 is a schematic illustration of a method of filling a sleeve with a hydration medium.

Turning now to FIG. 9, this figure provides a schematic representation of a fill method that includes an injection system 50. The urinary 10 may be docked or otherwise operatively connected to a hydration medium injection system or machine 50. The hydration medium injection system 50 may include a source 52 of hydration medium, which could be a reservoir or tank containing an amount of hydration medium 56. The hydration medium may be a foamed liquid. The system may include a conduit 58, one end 60 of which is connected to the source 52 of hydration medium and the end 62 of which is configured to be connected to the urinary catheter 10 so that hydration medium 56 can be injected into the cavity of the sleeve 22. For example, the end 62 of the conduit 58 may include a nozzle configured to be releasably connectable to the sleeve 22 or the introducer aid 30, if one is present. In another embodiment, the nozzle may be connected to the drainage member 20, wherein hydration medium is pumped through lumen 12*a* (FIGS. 3 and 4) of the catheter shaft 12 and the eyelets (FIGS. 1 and 3) into the cavity 28 of the sleeve 22. The system 50 also includes a pump or metering valves or other element 66 for moving/pumping hydration medium 56 so as to inject hydration medium 56 into the cavity of the sleeve 22.

In a method of making a catheter product, hydration medium 56, such as foamed liquid, is injected into the cavity of the sleeve 22 so that the hydration medium 56 is in contact with the catheter shaft 12. During the injection of the hydration medium 56, venting the air 68 out of the cavity of the sleeve 22 through at least one vent 42 located at the distal portion 26 of the sleeve 22. During the injection of hydration medium 42, air flow out of the vents may have a combined air flow of between about 1 milliliters per second and about 40 milliliters per second. In one embodiment, the vents allow a combined maximum air flow of about 40 milliliters per second. In another embodiment, the vents allow a combined air flow of at least about 1 milliliters per second. Furthermore, during injection of the hydration medium 56, the pressure within the cavity of the sleeve 22 does not exceed 6 bar. Alternatively, during the injection of the hydration medium 56 the pressure within the cavity of the sleeve 22 is between about 0.1 bar and about 6 bar. Furthermore, an injection pressure of the hydration medium 56 is between about 0.5 and about 4 bar. The at least one vents 42 and/or the injection pressure of the hydration medium 56 may be tailored or selected so that the pressure within the cavity sleeve is maintained within a desired range, such as the above discussed ranges. For example, the opening area of the vents and/or the injection pressure may be modified to control the pressure within the sleeve. Optionally, the hydration medium 56 may be injected into the cavity of the sleeve 22 at a flow rate of between about 1 L/hr and about 24 L/hr.

After the hydration medium 56 has been injected into the sleeve, the urinary catheter may be placed with a compartment of a package. The package may be sealed to seal urinary catheter within the compartment. The package may be a gas impermeable package, such as a package made from a gas impermeable material. Such package may be a foil package that is made from metal foil and polymer laminates.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

What is claimed is:

1. A method of making a catheter product that has a sleeve having a cavity wherein at least a portion of a catheter shaft of a urinary catheter is located within the cavity such that the sleeve surrounds the portion of catheter shaft, a distal portion of the sleeve is attached to a distal portion of the urinary catheter and a proximal portion of the sleeve is attached an introducer aid, the method comprising:

connecting a nozzle to the catheter product;

injecting a hydration medium from the nozzle and into the catheter product, wherein the hydration medium is injected into the cavity of the sleeve and is in contact with the catheter shaft; and during the injection of the hydration medium, venting air out of the cavity of the sleeve through at least one vent located at the distal portion of the sleeve.

2. The method of claim 1, wherein the sleeve is attached to the urinary catheter in at least one attachment location and the at least one vent is defined between the urinary catheter and a distal end of the sleeve.

3. The method of claim 2, wherein a drainage member located at a distal end of the catheter shaft and the distal portion of the sleeve is attached to the drainage member.

4. The method of claim 2, wherein the distal portion of the sleeve is attached to the catheter shaft.

5. The method of claim 1, wherein the at least one vent is located in a wall of the sleeve.

6. The method of claim 1, wherein the at least one vent comprises two vents.

7. The method of claim 1, wherein the at least one vent has a combined vent opening area of between about 30 square millimeters and about 40 square millimeters.

8. The method of claim 1, wherein the at least one vent has a combined air flow of between about 1 milliliters per second and about 40 milliliters per second.

9. The method of claim 1, wherein during injection of the hydration medium, pressure within the cavity of the sleeve does not exceed 6 bar.

10. The method of claim 9, wherein during injection of the hydration medium, the pressure within the cavity of the sleeve is between about 0.1 bar and about 6 bar.

11. The method of claim 1, wherein an injection pressure of the hydration medium is between about 0.5 and about 4 bar.

12. The method of claim 1, wherein the hydration medium is injected into the cavity at a flow rate of between about 1 L/hr and about 24 L/hr.

13. The method of claim 1, wherein the hydration medium is a foamed liquid.

14. The method of claim 1, further including placing the sleeve and catheter within a package.

15. The method of claim 1, wherein the introducer aid includes an opening in communication with the sleeve, and injecting hydration medium into the cavity of the sleeve includes injecting hydration medium through the opening in the introducer aid.

16. The method of claim 1, wherein the catheter shaft includes drainage eye in communication with a lumen of the catheter shaft, and injecting the hydration medium into the cavity includes injecting hydration medium into the lumen and through the drainage eyes into the cavity.

* * * * *